United States Patent [19]
Filhol

[11] Patent Number: 5,482,465
[45] Date of Patent: Jan. 9, 1996

[54] DENTAL PIN ASSEMBLY

[76] Inventor: Stuart J. Filhol, 2 Church Green, Witney, Oxon, OX8 6AW, United Kingdom

[21] Appl. No.: 211,914
[22] PCT Filed: Oct. 21, 1992
[86] PCT No.: PCT/GB92/01932
  § 371 Date: May 23, 1994
  § 102(e) Date: May 23, 1994
[87] PCT Pub. No.: WO93/07827
  PCT Pub. Date: Apr. 29, 1993

[30] Foreign Application Priority Data

Oct. 21, 1991 [GB] United Kingdom .............. 9122295

[51] Int. Cl.⁶ ........................................ A61C 5/04
[52] U.S. Cl. ................................................ 433/225
[58] Field of Search ........................... 433/220, 221, 433/225

[56] References Cited

U.S. PATENT DOCUMENTS

| | | | |
|---|---|---|---|
| 3,740,851 | 6/1973 | Weissman | 433/225 |
| 4,219,620 | 8/1980 | Carse | 433/225 |
| 4,451,237 | 5/1984 | Filhol | 433/225 |
| 4,500,296 | 2/1985 | Friedman | 433/225 |
| 4,553,942 | 11/1985 | Sutter | 433/225 |
| 4,655,711 | 4/1987 | Weissman | 433/225 |
| 4,728,292 | 3/1988 | Lustig et al. | 433/225 |
| 4,729,736 | 3/1988 | Weissman | 433/221 |
| 4,917,606 | 4/1990 | Miller | 433/225 |

FOREIGN PATENT DOCUMENTS

| | | |
|---|---|---|
| 0056198 | 7/1982 | European Pat. Off. . |
| 0076084 | 4/1983 | European Pat. Off. . |
| 0179599 | 4/1986 | European Pat. Off. . |
| 2316126 | 10/1973 | Germany . |

Primary Examiner—Nicholas D. Lucchesi
Attorney, Agent, or Firm—Ostrolenk, Faber, Gerb & Soffen

[57] ABSTRACT

A dental pin assembly comprises a dental pin holder and a dental pin. The dental pin comprises a threaded portion which has been made by rolling, and a shank portion which is slid into a longitudinal bore defined in the holder and is secured therein by distorting the shank portion or the bore or both into interengagement while the shank portion is in the bore.

19 Claims, 2 Drawing Sheets

DENTAL PIN ASSEMBLY

BACKGROUND OF THE INVENTION

This invention relates to a dental pin assembly which comprises a dental pin for anchoring dental superstructures e.g. caps, veneers, onto a tooth, and a dental pin holder to facilitate the handling of the dental pin by the dental surgeon.

In particular, the present invention relates to dental pin assemblies in which the dental pin is a threaded pin and is for self-tapping insertion into the dentine of the tooth. Such pins commonly have a threaded portion which is releasably connected to a shank portion through a low shear neck portion. The threaded portion of the pin is inserted into the dentine to a pre-determined level at which a resistance to rotation is established, and any rotation against this resistance then provides sufficient torque to shear the pin at the neck portion. Shearing of the neck portion leaves a portion of the pin projecting from the surface of the dentine to which a dental superstructure can be secured.

Prior art threaded pins have had their threaded portions formed by precision machining, with further machining to provide the low shear neck portion. A significant disadvantage with machining to form the threaded portion of the pin is that a large amount of raw material is wasted, and since the materials used to make dental pins tend to be very expensive the cost of manufacturing pins by this process is very high.

The small dimensions of dental pins necessitate the use of a dental pin holder to facilitate handling and fitting of the pin into the dentine of the tooth. These holders typically comprise a cylindrical body which has a longitudinal central bore into which the shank of the dental pin is slid and subsequently secured therein. The central bore can be open at both ends or closed at one end depending upon type of method used to secure the shank within the bore.

The shank can be releasably or permanently secured within the bore, but permanent securement is preferred since releasable attachments used in the past have proved to come undone during fitting of the dental pin. A wide variety of methods for permanently securing the shank of the dental pin within the bore of the dental holder are known, examples of which are described in GB 1482681, EP 179599 and EP 56198.

The holder can be part of a standard dental hand-piece to be used manually by the dental surgeon, or more commonly the holder is for releasable attachment to an automated device capable of rotating the entire dental pin assembly.

Once the dental pin has been sheared at the neck portion as described above, both the shank and the holder are disposed of. It is therefore desirable that the holder be made of a relatively cheap material, and that the volume of the shank is as small as possible to reduce the ultimate cost of the dental pin assembly as a whole.

SUMMARY OF THE INVENTION

According to the present invention, a dental pin assembly comprises a dental pin holder and a dental pin, wherein
the holder comprises a body that defines a longitudinal central bore for receiving the dental pin
and the dental pin comprises
a threaded portion for self-tapping insertion into a tooth,
a shank portion which is permanently secured within the bore of the holder and
a shearable neck portion interconnecting the threaded and shank portions, characterised in that
the dental pin has been formed from dentally acceptable wire of a substantially uniform diameter by rolling one end of the pin to form the threaded portion and by machining to form the shearable neck portion, and
the shank portion is permanently secured in the bore as a result of the shank portion or the bore or both having been permanently distorted into interengagement while the shank portion is in the bore.

The present invention also provides a method for making the dental pin assembly described above, wherein the method comprises the steps of
(1) making a dental pin by
forming the threaded portion of the pin by rolling one end of a piece of dentally acceptable wire of substantially uniform diameter,
leaving the other end of the piece of wire adjacent the formed threaded portion unrolled and substantially straight to form the shank portion of the pin, and
weakening the wire between the threaded and shank portions to form the shearable neck portion of the pin, and
(2) sliding the shank of the pin into the bore of the dental holder and permanently securing the shank therein by distorting the shank portion or the bore or both into interengagement.

Rolling is a well known technique used to physically deform lengths of metal into threaded structures. Basically the process involves rolling a length of metal, the stock, between at least two rollers. The rollers bear onto the stock with considerable force and deform the metal crystalline structure, and this results in the formation of a thread. Rolling therefore forms a thread without cutting away any metal from the original metal stock used. One consequence of rolling to form a thread is that an increase in the outer diameter of the metal stock is observed.

A rolling technique has been applied in the prior art to manufacture dental posts, as discussed in U.S. Pat. No. 4,729,736. The dental post made by this method comprises a lower portion having an intricate array of helices with parallel ridges or contours along its length.

In the present invention, a length of wire forms the stock that is to be rolled. The wire has a diameter generally in the range from 0.25 to 1 mm, and usually from 0.5 to 0.75 mm in practice. Known rolling, or coining, techniques are then used to deform part of the wire into the threaded lower portion of a dental pin.

As mentioned above, the outer diameter of the thread is greater after rolling than the diameter of the original piece of wire, and will usually be in the range 0.6 to 1 mm.

Rolling in this way can produce a pin having a threaded portion with 15 to 30 turns. Typically a number of around 20 turns is provided.

The length of the threaded portion is generally in the range 2 to 10 mm and usually in the range 4 to 5 mm.

The shank portion of the dental pin is not subjected to rolling, and therefore comprises a portion of the original piece of wire substantially unaltered. The length of the shank portion is in the range 5 to 25 mm.

The shearable neck portion interconnecting the threaded and shank portions is weakened by any suitable known method, e.g. cutting wire away at the respective place, or punching at that place from at least two directions using V-shaped punching tools. The neck portion has a break point of a standard strength to that known in the prior art.

The entire dental pin is manufactured from one material which must be acceptable for use in dentistry. Such materials tend to be rather expensive and include titanium, gold, and special graded stainless steels. Prior art methods of making dental pins involving machining the threaded portion of the pin are very expensive on account of the large amount of raw material cut away and therefore wasted.

In contrast, making the threaded portion of the dental pin by rolling does not cut away any of the expensive raw material but simply deforms it into a thread shape. This is a significant advantage over the prior art since it greatly cuts the cost of producing the dental pin, and therefore the final dental pin assembly.

Also, the pin can be made from wire that is much thinner than is required when the thread is to be made by machining in the normal way; this again cuts the cost of manufacturing such pins.

Because the wire is thin, it is essential that there should be an easy way of holding it for use, and the invention provides this.

The dental pin holder comprises a body which defines a longitudinal central bore. The shape of the body is typically cylindrical for convenience, so that the holder fits all the major tools already in use in the dental field.

The dental pin holder is made of metal or plastic material. It is important that the holder has a large profile and that it should be of a relatively strong material with quite a high density, to make it easy for the dental surgeon to handle. Metal dental holders tend robe preferred over plastic holders, not only because their properties are more suitable but also because they are more aesthetically pleasing to the eye of the dental surgeon as opposed to their plastic equivalent which tends to look cheap and inferior. Metals commonly used for dental pin holders include brass, aluminium, steel etc, of varying grades, i.e. cheaper metals than those used for the dental pin itself.

The bore of the holder is typically cylindrical in shape so as to receive the shank portion of the pin, but it may be of a different shape as long as the shank can be slid easily into it. The diameter of the bore is slightly larger than that of the shank portion which has substantially the same diameter as the original piece of wire.

The shank of the dental pin is slid into and permanently secured within the bore of the dental pin holder by permanently distorting the shank portion or the bore or both into interengagement.

When the holder is of a relatively ductile material, such as brass, a preferred method of permanently securing the shank within the bore of the holder comprises sliding the shank into the bore and then applying an external force, in the form of at least one punch or a stamp, to the holder at at least one longitudinally spaced apart position along the length of the holder corresponding to the position of the shank portion within the bore. The punch or stamp distorts the bore by causing the wall of the bore to be distorted inwards forming a projection, which interengages the shank portion and secures it within the bore. This can be due solely to a frictional force, or alternatively if a sufficiently strong punching force is used, the shank itself will also be distorted in such a way as to provide yet further securement of the shank within the holder. Such distortion of the shank will depend upon the positions at which the holder is punched, and this is described below.

The number of longitudinally spaced apart positions at which the holder is punched is one or more, and these should be chosen such that a stable secure fitting is provided. The holder is punched at least once, e.g. 1 to 4 times, at any one longitudinal position, and when it is punched more than once this is preferably done at substantially equiangular intervals around the holder, to provide secure fitting of the shank within the holder. Punching at any one longitudinal position can be offset with respect to that at other longitudinal positions, but should be arranged to give secure fitting of the shank, this is referred to as offset punching.

When using a punching force sufficient to distort both the holder and the shank, punching the holder from both sides at diametrically opposite positions, may cause the projection in the wall of the bore to extent into the shank portion, distorting it inwards so and providing a kind of latching means which secures the shank portion within the bore. Whereas, in an alternative embodiment involving punching once at each longitudinal position and at a place which is diametrically opposite longitudinally adjacent punches, the shank may be distorted into a concertina structure, with each fold of the concertina co-operating with its respective inwards projection in the bore of the holder. In this latter embodiment it is preferred that the bore has a larger transverse dimension with respect to the shank than in the former, standard, punching embodiment.

The punching is carried out by applying a force to a metal pin-type construction, which is desirably automated, so that fixing of the shank portion within the bore can be carried out very quickly. The amount of punching force necessary is dependent particularly upon the ductability of the holder; the overall properties of the holder and the shank portion; and on the surface area of the punch itself.

This "punching" method of securing the pin within the holder, as I shall call it, is preferred, since a short shank portion, as compared to the prior art, can be used depending on the position of punching, and this reduces the expense of manufacturing the dental pin assembly.

An alternative method of securement involves concertinaing the shank of the pin within the bore of the holder by the application of a force to the shank in a direction along the longitudinal axis of the shank.

The extremes of each fold of the concertina so formed interengage with the walls of the bore to provide a friction-fit hold of the shank within the bore. It is preferred that the transverse dimension of the bore is larger with respect to the shank than the standard "punching" method described earlier.

The force can be applied to the shank at either of its longitudinal ends. Firstly, considering its application to that end furthest from the threaded portion, which I shall call the far end of the shank/bore (the end of the shank/bore neighbouring the threaded portion shall be called the near end). The bore of the holder is at least temporarily open at both ends. The shank is slid into the bore and is fixed therein by, e.g., the "punching" method described above, carried out at the near end of the bore. This prevents the shank being pushed out of the bore while the force is applied to its far end. The force is then applied to the far end of the shank, and causes the shank to concertina.

Secondly, considering the application of the force to the near end of the shank. This involves the use of a dental holder having a bore which has a stop at one end, formed either during its manufacture, e.g. a bore with a closed end or a step in the wall of the bore, or by the insertion of a stopper at one end. The shank portion of the pin is slid into the bore of the holder to a stop, e.g. until it contacts the closed end of the bore. The force is then applied, and the shank is forced up against the stop and into a concertina structure. The force itself can be applied at a point intermediate the shank and threaded portions, or alternatively it can be applied at the end of the threaded portion. In the latter case, it may be necessary to protect the threaded portion from deformation due to the application of the force, and this can be done, for example, by sliding a protective sleeve over the threaded portion which is closed at that end to which the force is to be applied.

To aid concertina-ing of the shank, it is possible to partially concertina the shank prior to its insertion into the holder, and this can be done by any suitable known method, e.g. placing the wire longitudinally between combs arranged to have inter-locking teeth, and pushing the combs together to distort the wire.

BRIEF DESCRIPTION OF THE DRAWINGS

The present invention is now further illustrated by way of reference to the following figures.

DETAILED DESCRIPTION OF THE DRAWINGS

Figure 1:
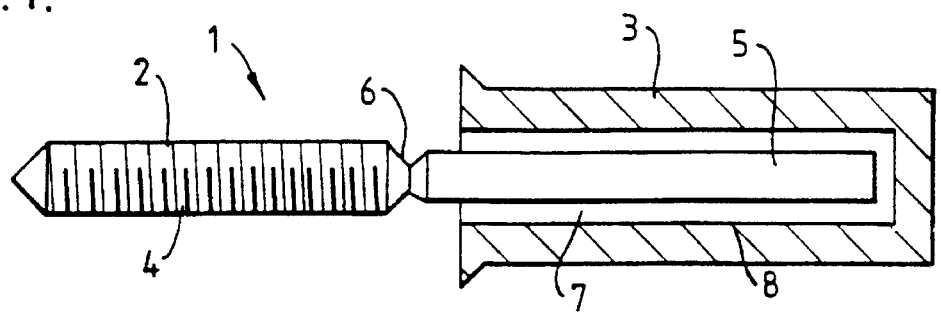
FIG. 1 is a transverse view of the dental pin assembly according to the present invention.

FIG. 1 shows a dental pin assembly (1) comprising a dental pin (2) and a dental pin holder (3).

The dental pin comprises a threaded portion (4) which has been made by a rolling method, a shank portion (5) and interconnecting the threaded and shank portions a shearable neck portion (6) which has been made by weakening of the wire.

The shank portion of the pin is slid into a longitudinal central bore (7) of the dental pin holder; the bore has walls (8).

Figure 2:
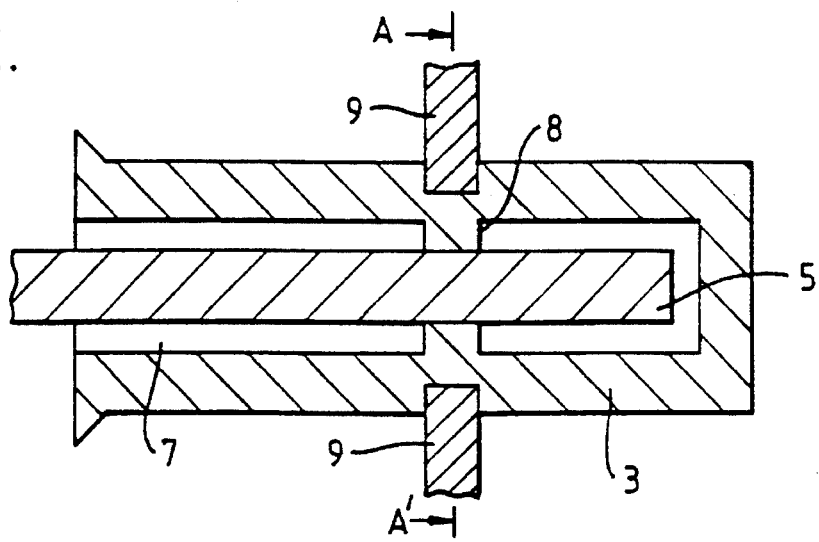
FIG. 2 is a transverse cross-sectional view of the shank of the dental pin secured within the holder by the "punching" method.

FIG. 2 shows an enlarged view of the dental pin holder (3) and the shank (5) secured within the bore (7) of the holder by the "punching" method. The punching shown here is by the application of force to two pairs of punches (9), the punches making up each pair being arranged diametrically opposite to each other, and this causes distortion of the wall of the bore (8) alone, as shown here, so relying on a friction-fit hold of the shank, or together with the shank.

Figure 3A:
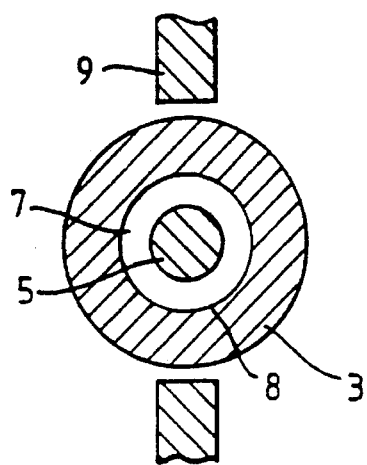
FIGS. 3A and 3B are two cross-sections taken along A–A' as shown in FIG. 2.
Figure 3B:
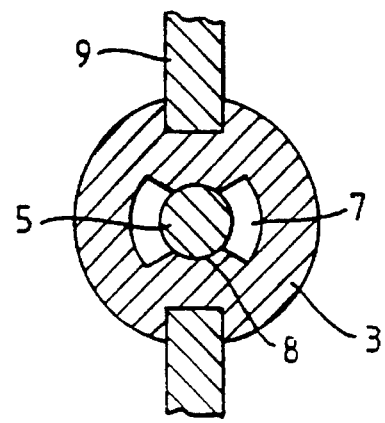

FIG. 3A shows the dental pin assembly prior to punching using two punches (9) diametrically opposite each other. FIG. 3B shows the same assembly after punching; the wall of the bore (8) has been inwardly distorted to trap the shank (5) within the holder (3).

Figure 4:
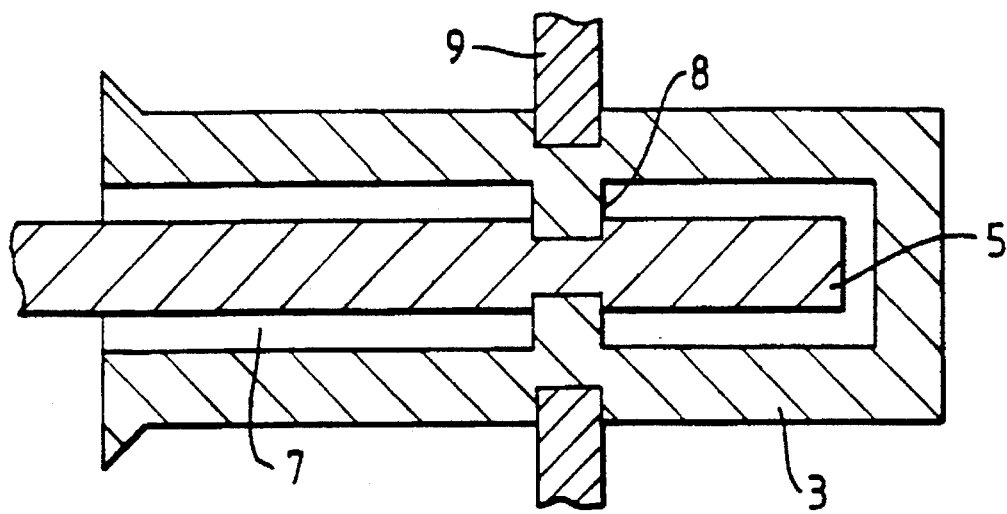
FIG. 4 is a further transverse cross-sectional view of the shank of the dental pin secured within the bore of "punching" method.

FIG. 4 shows an enlarged view of the dental pin holder (3), and the shank (5) secured within the bore (7) of the holder by the "punching" method. In this case, the force applied to each of the punches was sufficient to cause distortion of both the wall of the bore and the shank of the pin, so that the projections (8) extend into the shank portion (5).

Figure 5:
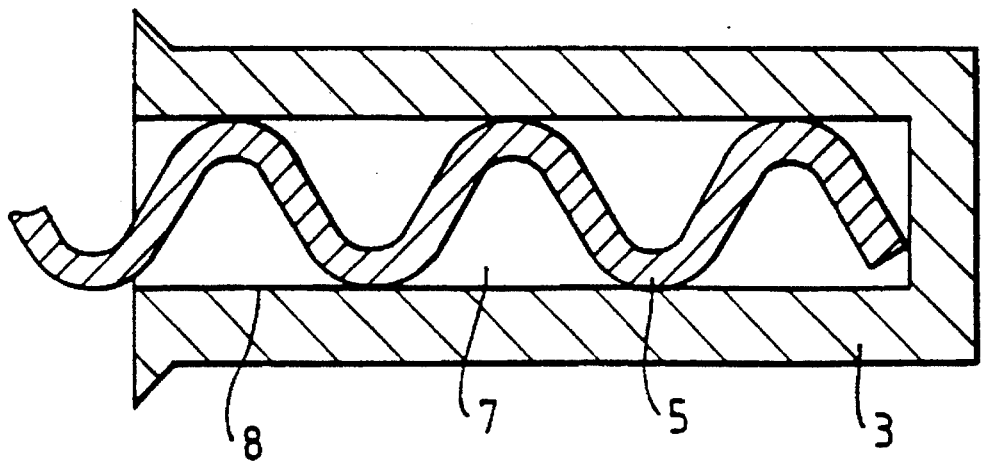
FIG. 5 is a transverse cross-sectional view of the shank of the dental pin secured within the dental pin holder by the "concertina" method.

FIG. 5 shows an enlarged view of the dental pin holder (3) with the shank (5) of the dental pin secured within the bore (7) of the dental pin holder by the "concertina" method.

I claim:

1. A dental pin assembly comprising a dental pin holder and a dental pin, wherein the holder comprises a body that defines a longitudinal central bore for receiving the dental pin and the dental pin comprises a dentally acceptable wire having a threaded portion for self-tapping insertion into a tooth having a rolled thread and a first cross section, a shank portion having a smaller cross section than said first cross section and a shearable neck portion interconnecting the threaded and shank portions, wherein the shank portion is permanently secured in the bore by a distorted portion formed on at least one of the shank portion and the holder, said distorted portion engaging said shank portion and said holder with each other.

2. A dental pin assembly according to claim 1, wherein the shank portion of the dental pin has a diameter from 0.25 to 1 mm.

3. A dental pin assembly according to claim 1 wherein the threaded portion of the dental pin has an outer diameter from 0.6 to 1 mm.

4. A dental pin assembly according to claim 1 wherein said distorted portion comprises at least one projection which extends into the bore and interengages with the shank portion thereby securing the shank portion within the bore.

5. A dental pin assembly according to claim 4 wherein said distorted portion comprises at least two said projections at a given longitudinal position along the bore arranged at substantially equiangular intervals around the bore.

6. A dental pin assembly according to claim 4 having wherein the distorted portion comprises at least two said projections disposed at different longitudinal positions offset with respect to one another.

7. A dental pin assembly according to claim 4 to wherein the at least one projection extends into the shank portion.

8. A dental pin assembly according to claim 1 wherein the shank portion comprises a concertina which interengages the wall of the bore thereby securing the shank portion within the bore.

9. A method for making a dental pin assembly comprising a dental pin holder and a dental pin, wherein the holder comprises a body that defines a longitudinal central bore for receiving the dental pin and the dental pin comprises a threaded portion for self-tapping insertion into a tooth, a shank portion and a shearable neck portion interconnecting the threaded and shank portions, the method comprising the steps of (1) making the dental pin by forming the threaded portion of the pin by rolling one end of a piece of dentally acceptable wire of substantially uniform diameter, leaving the other end of the piece of wire adjacent the formed threaded portion unrolled and substantially straight to form the shank portion of the pin, and weakening the wire between the threaded and shank portions to form the shearable neck portion of the pin, and (2) sliding the shank portion of the pin into the bore of the dental holder and (3) permanently securing the shank portion therein by distorting at least one of the shank portion and the holder into interengagements with the other.

10. A method according to claim 9 comprising distorting the bore by applying an external force to the holder at a longitudinal position along the length of the holder to form at least one projection in the wall of the bore which extends into the bore and interengages with the shank portion thereby securing the shank portion in the bore.

11. A method according to claim 10 wherein the external force is sufficient to cause the projection to extend into the shank portion.

12. A method according to claim 10 wherein the external force is applied by a punch.

13. A method according to claim 10 wherein said external force is applied to more than one longitudinal position along the length of the holder.

14. The method of claim 13 in which the wire has a diameter of 0.5 to 0.75 mm and 4 to 5 mm of the wire from said one end is rolled to produce a threaded portion with about 20 turns.

15. A method according to claim 9 comprising distoring the shank portion by applying an external force to the shank protion in a direction along the longitudinal axis of the shank portion to cause it to concertina and interengage the wall of the bore thereby securing the shank portion in the bore.

16. A method according to claim 15 wherein the bore comprises a stop, and the force is applied to concertina the shank portion against the stop.

17. A method according to claim 9 said wire has a diameter of from 0.25 to 1 mm and 2–10 mm from said one end is rolled to form a threaded portion having 15–30 turns.

18. A method for making a dental pin assembly comprising a dental pin holder and dental pin, wherein the holder comprises a body that defines a longitudinal central bore for receiving the dental pin and the dental pin comprises a dentally acceptable wire having a threaded portion for self-tapping insertion into a tooth having a rolled thread and a first cross-section, a shank portion having a smaller cross section than said first cross section and a shearable neck portion interconnecting said threaded and shank portions, the method comprising the steps of providing said dental pin, sliding the shank portion of the pin into the bore of the dental holder and distorting at least one of the shank portion and the holder into interengagement with each other to thereby permanently secure the shank portion in the bore.

19. The method of claim 18 wherein the shank portion of the dental pin has a diameter of from 0.25 to 1 mm, the threaded portion of the dental pin has an outer diameter of 0.6 to 1 mm and the distorting is effected by employing an external force to the holder so as to form at least one projection in the wall of the bore which extends into the bore and interengages with the shank portion.

\* \* \* \* \*